United States Patent [19]

Dockner et al.

[11] 4,052,384

[45] Oct. 4, 1977

[54] MANUFACTURE OF AZIRIDINOCARBOXYLIC ACID ESTERS

[75] Inventors: Toni Dockner, Meckenheim; Albrecht Wallis; Rolf Fikentscher, both of Ludwigshafen; Rainer Thomas, Frankenthal; Reinhard Herzog, Ludwigshafen, all of Germany

[73] Assignee: BASF Aktiengesellschaft, Ludwigshafen, Germany

[21] Appl. No.: 676,573

[22] Filed: Apr. 13, 1976

[30] Foreign Application Priority Data

May 16, 1975 Germany .............................. 2521859

[51] Int. Cl.$^2$ .................. C07D 203/18; C07D 295/14
[52] U.S. Cl. ............................. 260/239 E; 8/115.5; 8/128 A; 8/191; 260/75 N
[58] Field of Search .................................. 260/239 E

[56] References Cited

U.S. PATENT DOCUMENTS 3,336,294   8/1967   Miller et al. ..................... 260/239 E

FOREIGN PATENT DOCUMENTS 2,334,656   1/1975   Germany ......................... 260/239 E

OTHER PUBLICATIONS

Groggins, Unit Processes in Organic Synthesis, (Fifth Edition, New York, 1958), pp. 711-713.
Blagonrauova et al., Chem. Abstracts, vol. 35, col. 5731 (1941).
Groggins, Unit Processes in Organic Synthesis, (Third edition, New York, 1947), p. 637.

*Primary Examiner*—Alton D. Rollins
*Attorney, Agent, or Firm*—Keil, Thompson & Shurtleff

[57] ABSTRACT

Aziridinocarboxylic acid esters of polyols are manufactured by trans-esterification of the corresponding esters of lower alcohols, using magnesium oxide or calcium oxide as the trans-esterification catalyst; this method gives a higher yield and a purer product.

5 Claims, No Drawings

MANUFACTURE OF AZIRIDINOCARBOXYLIC ACID ESTERS

The present invention relates to an improved process for the manufacture of aziridinocarboxylic acid esters of the general formula

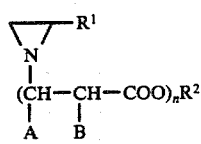
(I)

where A is hydrogen, methyl or the $n$th part of the group $(-COO)_n R^2$, B is hydrogen or methyl, $R^1$ is hydrogen or a short-chain alkyl, eg. of 1 to 5 carbon atoms, and $R^2$ is the $n$-valent radical of an alcohol of at least 2 carbon atoms which carries at least $n$ hydroxyl groups, and $n$ is an integer which is at least 2, preferably from 2 to 5, and especially 2.

The process to which the improvement relates comprises the reaction of compounds of the general formula (I), where $R^2$ is a radical of methanol, ethanol or propanol, with any other organic compound which possesses at least two alcoholic OH groups and is also inert under the trans-esterification conditions, in the presence of a basic trans-esterification catalyst, and removing methanol, ethanol or propanol, by distillation, from the esterification equilibrium.

As may be seen, the compounds (I) include esters of the following acids substituted in the 3-position by an aziridine radical (ie. an ethyleneimino radical): propionic acid, isobutyric acid, succinic acid, 2-methylsuccinic acid, n-butyric acid and 2-methylbutyric acid.

Where n is 2 and A is the nth part, i.e. half, of the group $(-COO)_{nR^2}$, the compounds (I) can be polymeric ethyleneiminosuccinic acid esters which are represented by the more detailed formula (II)

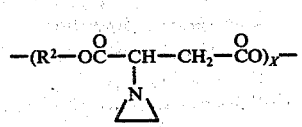
(II)

where X is the degree of polymerization which may, eg., assume values from 5 to 5,000. The end groups of the chains are hydroxyl, carboxyl or ester groups.

Aziridinocarboxylic acid esters can be manufactured by esterifying α-unsaturated carboxylic acids, eg. acrylic acid, methacrylic acid and crotonic acid, with a suitable alcohol, followed by addition reaction of ethyleneimine at the double bond of the ester; this method is described in, eg., U.S. Pat. Nos. 2,569,200 and 3,453,242. According to a publication by R. Huttel in the journal "Fette, Seifen, Anstrichmittel", 64, 107-110 (1962), the said reaction has also been investigated using unsaturated polyesters, in which case polyethyleneimino-polyesters are obtained, which are of value as, eg., paint ingredients, plastics and textile finishes.

This inherently simple conventional method has, inter alia, the following disadvantages:

1. In spite of careful use of acid catalysis (with sulfuric acid), and even when working in the presence of stabilizers, eg. phenothiazine or hydroquinone, and using a low-boiling entraining agent, undesirable polymerization at the double bond can, in many cases, not be prevented entirely.

2. Removal or neutralization of the acid (added as transesterification catalyst), which, as is well known, must be carried out prior to the reaction with alkyleneimines, can only be achieved with difficulty; any acid left causes the end products, containing aziridine groups, to be unstable on storage.

3. The reaction of the unsaturated polyester with ethyleneimine takes place quantitatively only if an excess of ethyleneimine is present, and the free ethyleneimine which then remains in the resin is difficult to remove quantitatively. A much better method of manufacturing such aziridinocarboxylic acid esters employs the trans-esterification reaction of the relatively easily accessible methyl, ethyl or propyl ester of β-aziridinocarboxylic acid with an appropriate alcohol, in accordance with the equation:

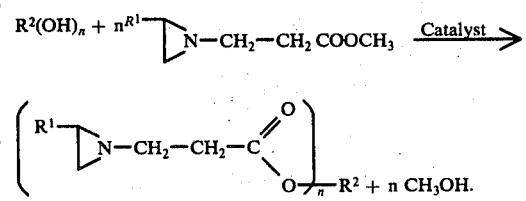

In this equation, $R^1$ is hydrogen or lower alkyl of 1 to 5, preferably 1, carbon atom, and $n$ is an integer greater than 1, preferably from 2 to 5, and especially 2.

In principle, this trans-esterification process is disclosed, for aziridinopropionic acid esters, in French Patent 1,544,210. However, if the trans-esterification is carried out in the manner described in the said patent, with sodium alcoholate as the catalyst, the desired aziridinopropionic acid esters are only obtained in a very impure form and in very poor yield. Particularly in the case of esters of alcohols of relatively high molecular weight, or polymeric esters, the process fails.

Though attempts have been made to displace the equilibrium reaction towards the desired ester by distilling off the methanol liberated, experience has shown that this is not completely successful; alcohols of relatively high molecular weight, in particular, tenaciously retain methanol, even though the latter is volatile, and the result is incomplete conversion.

In addition, the high temperatures which, according to the French Patent, are required even when using lower alcohols (from 150° to 170° C), frequently destroy at least a part of the reaction product, and a substantial part of the aziridonocarboxylic acid methyl ester employed distils off with the methanol.

As a result, the conventional process requires a large excess of methyl ester, which is separated off at the end of the reaction. Apart from the fact that the use of a large excess of the relatively expensive methyl ester is uneconomical, the quantitative removal of this ester from reaction products which in some cases are extremely viscous (and are frequently solid at room temperature) presents great difficulties. On the other hand, quantitative removal of the aziridinocarboxylic acid methyl ester from the products obtained is essential for toxicological reasons.

German Published Application No. 2,334,656 has already disclosed that a process of the above type offers certain advantages, and can be carried out more successfully than hitherto, if the reaction is carried out in the presence of a paraffin hydrocarbon of 7 to 12 carbon atoms and methanol, ethanol or propanol is distilled off with the said hydrocarbon, and if the trans-esterification catalyst used is, preferably, a tertiary amine or the aziridinocarboxylic acid ester itself which is present.

It is true that the use of tertiary amines offers considerable advantages over the use of alkali metal alcoholates as trans-esterification catalysts, but the process still suffers from some shortcomings, i.e. the trans-esterification is still accompanied by objectionable side-reactions. It is not entirely possible to prevent some of the aziridine rings from being split off, with formation of the corresponding unsaturated esters, which in turn polymerize. This produces an undesirable increase in the viscosity of the reaction mixture and the content of chemcially bonded aziridine rings in the reaction product decreases. Furthermore, the reaction mixture discolors. Finally, reproducible results cannot be obtained. Another difficulty is that tertiary amines have proved to be inactive as catalysts when the trans-esterification is carried out with alcohols having molecular weights greater than 1,000.

It is an object of the present invention to provide a process which reproducibly gives purer and less discolored end products of the formula I, is very simple and economical, and gives high yields.

We have found that this object is achieved if, in a process for the manufacture of compounds of the general formula I

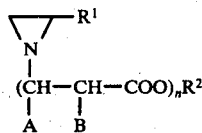

(I)

where A is hydrogen, methyl or the nth part of the group $(-COO)_n R^2$, B is hydrogen or methyl, $R^1$ is hydrogen or alkyl of 1 to 5 carbon atoms and $R^2$ is the $n$-valent radical of an alcohol of at least 2 carbon atoms which contains at least $n$ hydroxyl groups, and $n$ is an integer not less than 2, by trans-esterification of compounds of the general formula (I), where $R^2$ is a radical of methanol, ethanol or propanol, with an alcohol of at least 2 carbon atoms and containing at least $n$ hydroxyl groups, in the presence of a basic trans-esterification catalyst, and removal of the resulting methanol, ethanol or propanol from the esterification equilibrium by distillation, either magnesium oxide or calcium oxide is employed as the trans-esterification catalyst.

It is true that magnesium oxide and calcium oxide are known as trans-esterification catalysts, as are numerous other substances, but they have not previously been employed for the trans-esterification of aziridinocarboxylic acid esters. Furthermore, it was not to be expected that they would produce a special effect, particularly since other basic catalysts, e.g. alkali alcoholates, have not proved particularly successful. It is all the more surprising to find that when magnesium oxide and calcium oxide are employed in accordance with the invention, they result in a very big improvement in yield, color and purity of the end product and, when used as fixed bed catalysts, enable the process to be greatly simplified. Whereas in the case of the trans-esterification of aziridinopropionic acid methyl ester with diols or polyols of fairly high molecular weight, in the presence of the conventional catalysts, the trans-esterification product exhibits considerable variations in viscosity, color number and amount of ethyleneimine eliminated, magnesium oxide and calcium oxide have no effect on the viscosity and color number, even when used in relatively large amounts. The products obtained are more reactive because of their higher aziridine content, they can be processed more easily because of their lower viscosity and greater homogeneity and they are less discolored because side-reactions have been substantially suppressed.

The above remarks apply particularly if the methanol, ethanol or propanol produced in the reaction is continuously distilled off azeotropically, using paraffin hydrocarbons of 7 to 12 carbon atoms as the entraining agent.

The valency of a radical (cf. definition of $R^2$) means the number of valency bonds (linkage points) by which the radical is bonded to the remainder of the molecule.

Examples of suitable alcohols of at least 2 carbon atoms containing at least n hydroxyl groups are: aliphatic dihydric or higher polyhydric alcohols, eg. ethylene glycol, diglycol, triglycol, propylene glycol, butanediol, hexanediol, decanediol, trimethlolpropane, glycerol, pentaerythritol, sorbitol, polyethylene glycol ether, polypropylene glycol ether, polytetrahydrofuran, copolymers and block polymers of ethylene oxide, propylene oxide and tetrahydrofuran, and the like; oxyalkylated alcohols contaning n hydroxyl groups, e.g. reaction products of the above alcohols with ethylene oxide and/or propylene oxide; oxyalkylated amines, i.e. reaction products of ammonia or primary amines with ethylene oxide and/or propylene oxide, e.g. ethyldiethanolamine, triisopropanolamine and oxyalkylation products of, e.g., the following amines: ethylenediamine, diethylenetriamine, dipropylenetriamine, polyethyleneimine, polyamidoamines, stearylamine, decylenediamine and the like; oligomers or polymers containing any number of OH groups, for example polyesters (with free OH groups), e.g. polyesters of trimethylolpropane + adipic acid, polyurethanes and the like; and also natural materials, e.g. cellulose, starch, sugars and their oxyalkylation products.

It follows from the nature of the alcohols, containing n hydroxyl groups, which have been mentioned above that it is virtually impossible to specify an upper limit for $n$. In most cases, however, $n$ is from 2 to 5, and especially 2.

Ethylene glycol, 1,2-propylene glycol and 1,4-butylene glycol and their polyethers in which the degree of polymerization is from 2 to 100, preferably from 2 to 28, are preferred.

The preferred alcohol component of the aziridinocarboxylic acid ester employed as the starting material for the trans-esterification reaction is methanol, its advantages being a low boiling point, low molecular weight, cheapness and above all its ability to form azeotropes of advantageous composition and advantageous boiling point with hydrocarbons, eg. with octane and decane. In principle, however, ethanol or propanol can also be used.

The process of the invention is carried out essentially in the absence of water; however, small amounts of water in general do not interfere. The amount of magnesium oxide or calcium oxide to be used is not critical; in general, from 0.05 to 3% by weight, preferably from 0.1 to 2% by weight, based on the amount of reaction mixture, suffices. Larger amounts are not detrimental but as a rule are not advantageous either.

The trans-esterification can also be effected by circulating the reaction mixture, by pumping, over the catalyst (calcium oxide or magnesium oxide) arranged as a fixed bed; this dispenses with the difficult and expensive filtration of the product.

The trans-esterification is carried out at from 100° to 150° C, especially from 120° to 145° C, as a rule under atmospheric pressure. It can also be carried out under reduced pressure but this is unnecessary if an entraining agent for the lower alcohols to be removed is employed.

The reaction of aziridinodicarboxylic acid esters, e.g. aziridinosuccinic acid dimethyl ester, with a glycol produces polyesters which are substituted by the reactive ethyleneimino group. In the transesterification of aziridinodicarboxylic acid esters with polyols containing more than two OH groups, at least 1 mole of polyol is employed per mole of dicarboxylic acid, to avoid the formation of insoluble products by crosslinking. The end products may thus still contain a large number of free hydroxyl groups.

The end products, above all the reaction products of polyalkylene glycol ethers with aziridinomonocarboxylic acid esters, are used as, e.g., textile finishes, especially for the shrink-resist and wrinkle-resist finishing of wool. The highly reactive azidirine compounds form a resin film on the fibers and may react with the thiol groups and amide groups of the wool. Because of the increased aziridine content of the products obtainable according to the invention, the reactivity of the products is so great that wool can be provided with a reproducible shrink-resist non-felting finish with this product even before dyeing.

Another application of the products in the textile field consists in rendering polyamide fibers hydrophilic. For this application, the aziridinocarboxylic acid esters of polyethylene oxides are preferred. On the other hand, for finishing wool the reaction products of polytetrahydrofuran are preferred, since they at the same time impart a pleasant hand to the wool. Other fields of use are tanning of hides to produce leather, and quite generally all applications where polymer chains containing acidic hydrogen have to be crosslinked.

Examples of suitable end products are:

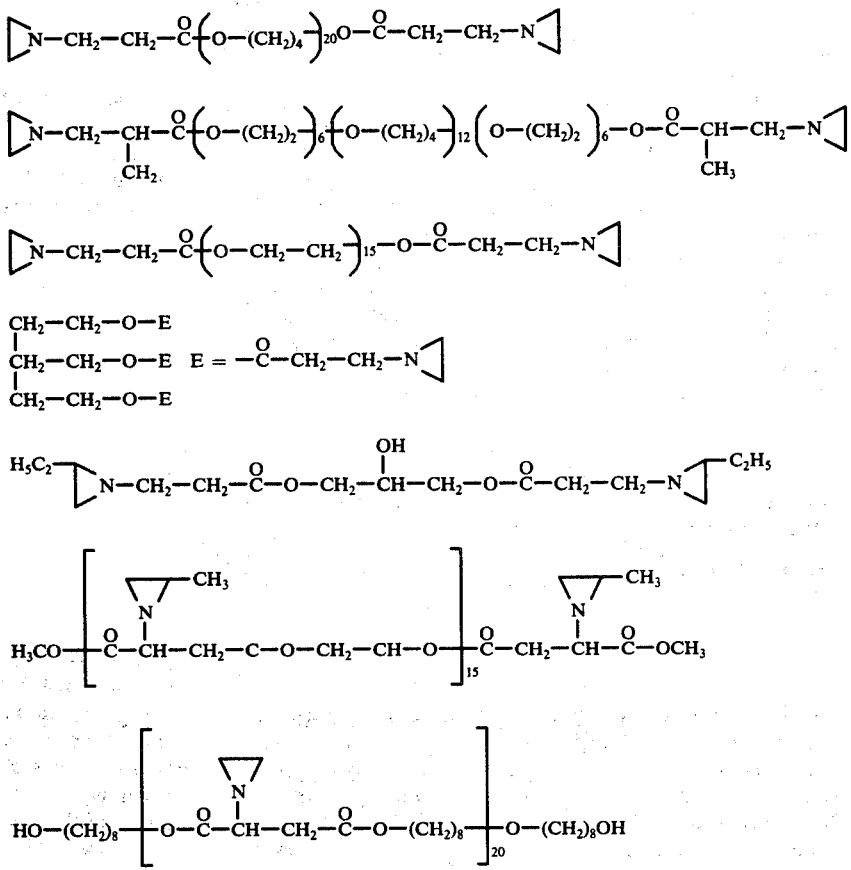

In the Examples, parts, percentages and ppm are by weight.

EXAMPLES 1. 1,000 parts of polytetrahydrofuran (PTHF) of average molecular weight 2,000, 220 parts of octane, 135 parts of β-aziridinopropionic acid methyl ester and (a) 10 parts, (b) 20 parts or (c) 50 parts of CaO powder are introduced into a heated vessel, equipped with a stirrer and a superposed condenser and separator, and are reacted at a bottoms temperature of 112° – 150° C. The course of the reaction is followed by observing the amount of methanol distilled off. During the trans-esterification, 90 – 95% of the calculated amount of methanol are obtained in the separator, the methanol containing 20% of dissolved octane.

The Table which follows shows the reaction times and reaction temperatures, viscosities, color numbers and aziridine-N content, in %, of the solvent-free end product, and the amount of ethyleneimine, in ppm, split off from the aziridinopropionic acid esters and found in the methanol-octane mixture which was distilled off.

Table

| Experiment | Reaction temp. °C | Reaction time | Viscosity in cp/60° (Höppler falling ball method) | Iodine color number | Ethyleneimine in ppm based on distillate | Aziridine nitrogen in %, based on residue (calculated: 1.2 %) |
| --- | --- | --- | --- | --- | --- | --- |
| a | 138–147 | 6 hours | 226 | 22/26 | 5 | 1.15 |
| b | 136–146 | 4 ¼ hours | 241 | 60/70 | 5 | 1.16 |
| c | 132–145 | 3 ¼ hours | 245 | 70/90 | 5 | 1.2 |

In the Comparitive Experiment which follows, the CaO was replaced by a) 10 parts, b) 20 parts and c) 50 parts of sodiummethylate. The Table which follows shows the values found in the case of these trans-esterifications.

| Experiment | Reaction temp. °C | Reaction time | Viscosity in cp/60° (Höppler falling ball method) | Iodine color number | Aziridine Ethyleneimine in %, based on distillate | nitrogen in %, based on residue (calculated: 1.2%) |
| --- | --- | --- | --- | --- | --- | --- |
| a | 112–140 | 2 hours | 587.8 | 90/120 | 4.18 | 1.00 |
| b | 112 14 137 | 50 mins | 3,075 | 90/120 | 3.9 | 0.88 |
| c | 112–128 | 40 mins | not measurable | 120/150 | 4.9 | 0.89 |

2. 1,500 parts of polytetrahydrofuran of average molecular weight 2,000, 206 parts of β-aziridinopropionic acid methyl ester and 330 parts of octane are introduced into a heated vessel equipped with a stirrer and a superposed condenser and separator. This mixture is circulated by means of a pump through a heated tube which is filled with 250 g of CaO lumps about 5 mm in diameter, and back again into the flask. The reaction takes place at from 135° to 145° C in the CaO-filled tube and the methanol formed is collected in the separator in an amount of 90–95% of theory.

The Table gives the analytical results obtained.

| Reaction temp. °C | Reaction time | Viscosity in cp/60° (Höppler falling ball method) | Color number | Ethyleneimine in ppm, based on distillate | Aziridine-N in % (calc. 1.2%), based on residue |
| --- | --- | --- | --- | --- | --- |
| 135–145 | 10 hours | 256 | 7/9 | 6 | 1.02 |

3. Using the same experimental apparatus as described in Example 1, 338.5 parts of β-aziridinopropionic acid methyl ester and 1,875 parts of polyethylene oxide of average molecular weight 1,500 are transesterified in the presence of 550 parts of octane and 57.5 parts of ground CaO, whilst at the same time separating off the methanol by distillation. At a bottoms temperature of 121°–125° C, the reaction time is 11 hours.

Aziridine-N: found: 1.56%, calc.: 1.65%, based on residue.

4. 561 parts of aziridinosuccinic acid dimethylester are transesterified with 162 parts of butanediol and 241 parts of trimethylolpropane in the presence of 300 parts of octane and 10 parts of ground CaO. The reaction time is 5 hours and the reaction temperature is 109°–122° C.

Aziridine-N: calc.: 5.4%; found: 4.29%, based on residue.

The trans-esterification product can be used as a crosslinking agent for polymers contianing carboxyl groups.

5. 645 parts of β-aziridinopropionic acid methyl ester are transesterified with 225 parts of butanediol in 400 parts of octane and 10 parts of ground CaO. At a reaction temperature of 118°–131° C, the reaction time is 4 hours. After distilling off the octane, 675 parts of butanediol bis-(β-aziridinopropionate), ie. 95% of theory, are obtained.

Aziridine-N: calc.: 9.85%; found: 9.67%.

Boiling point 170°–175° C/0.4 mm Hg.

The product can also be employed as a crosslinking agent.

We claim:

1. An improved process for the manufacture of aziridinocarboxylic acid esters of the general formula

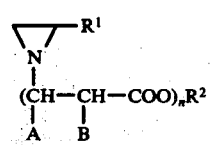

(I)

where A is hydrogen, methyl or the nth part of the group (—COO)$_n$R$^2$, B is hydrogen or methyl, R$^1$ is hydrogen or alkyl of 1 to 5 carbon atoms and R$^2$ is the n-valent radical of an alcohol of at least 2 carbon atoms which contains at least n hydroxyl groups, and n is an integer not less than 2, by trans-esterification of compounds of the general formula (I), where R$^2$ is a radical of methanol, ethanol or propanol, with an alcohol of at least 2 carbon atoms and containing at least n hydroxyl groups, in the presence of a basic trans-esterification catalyst, and removal of the resulting methanol, ethanol or propanol from the esterification equilibrium by distillation, wherein the improvement comprises using magnesium oxide or calcium oxide as the trans-esterification catalyst.

2. An improved process as set forth in claim 1, wherein the methanol, ethanol or propanol produced by trans-esterification is distilled off azeotropically with a paraffin hydrocarbon of 7 to 12 carbon atoms as the entraining agent.

3. An improved process as set forth in claim 1, wherein the compound of the general formula (I) which is prepared is a polymeric ester of ethyleneiminosuccinic acid or ethyleneiminomethylsuccinic acid.

4. An improved process as set forth in claim 1, wherein the alcohol containing n hydroxyl groups is ethylene glycol, 1,2-propylene glycol or 1,4-butylene glycol or a polyether thereof, in which the degree of polymerization is from 2 to 28.

5. A improved process as set forth in claim 1 wherein said trans-esterification catalyst is calcium oxide.

* * * * *